(12) United States Patent
Grez et al.

(10) Patent No.: US 8,425,133 B2
(45) Date of Patent: Apr. 23, 2013

(54) DISCRETE-AMOUNT FLUID-DISPENSING SYSTEM FOR A PERSONAL CARE DEVICE

(75) Inventors: Joseph W. Grez, North Bend, WA (US); Gerardus Joannes Henricus Roddeman, Son en Breugel (NL); Johannes Cornelius Antonius Muller, Bladel (NL); Dannis Michel Brouwer, Eindhoven (NL); Fridtjof Bremer, Ravenstein (NL); Robert Cornelis Henricus Boereboom, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1184 days.

(21) Appl. No.: 10/545,813

(22) PCT Filed: Dec. 3, 2003

(86) PCT No.: PCT/IB03/05643
§ 371 (c)(1),
(2), (4) Date: Nov. 14, 2005

(87) PCT Pub. No.: WO2004/056287
PCT Pub. Date: Jul. 8, 2004

(65) Prior Publication Data
US 2006/0159509 A1    Jul. 20, 2006

Related U.S. Application Data

(60) Provisional application No. 60/435,485, filed on Dec. 19, 2002.

(51) Int. Cl.
*A46B 11/00* (2006.01)
(52) U.S. Cl.
USPC ............................ 401/123; 401/126; 401/118

(58) Field of Classification Search .................. 401/123, 401/126, 129, 118, 119, 132–135, 282, 268, 401/270, 143, 152, 156, 163, 165, 171, 176, 401/178, 179, 181; 222/94, 95; 206/222, 206/528, 531, 532, 534.1, 535; 221/25, 71; 433/89
See application file for complete search history.

(56) References Cited

U.S. PATENT DOCUMENTS

| | | | | |
|---|---|---|---|---|
| 3,261,367 A | * | 7/1966 | Pickering | 401/135 |
| 4,090,642 A | * | 5/1978 | Baker | 222/94 |
| 4,817,800 A | * | 4/1989 | Williams et al. | 206/484 |

(Continued)

FOREIGN PATENT DOCUMENTS

| | | |
|---|---|---|
| DE | 3522459 A1 | 1/1987 |
| DE | 4238421 A1 | 5/1994 |

(Continued)

*Primary Examiner* — David Walczak
*Assistant Examiner* — Jennifer C Chiang

(57) ABSTRACT

The fluid-dispensing system is used in a personal care appliance, such as a power toothbrush. The dispensing system includes a strip of discrete, fluid-containing packets, a compressible sealing member and a hollow needle for puncturing the packets, the hollow needle being connected to a workpiece such as a brushhead via a connecting line. An actuation assembly includes a piston which moves successive packets against the sealing member, initially sealing the packet thereto. Further pressure results in compression of the sealing member and puncturing of the packet by the needle, with fluid being forced by piston pressure from the packet into the hollow needle and then to the connecting line for delivery to the workpiece.

10 Claims, 7 Drawing Sheets

U.S. PATENT DOCUMENTS

| | | | |
|---|---|---|---|
| 4,963,046 A * | 10/1990 | Eguchi | 401/160 |
| 5,189,751 A | 3/1993 | Giuliani et al. | |
| 5,207,217 A * | 5/1993 | Cocozza et al. | 128/203.21 |
| 5,339,839 A * | 8/1994 | Forcelledo et al. | 132/114 |
| 5,349,947 A * | 9/1994 | Newhouse et al. | 206/531 |
| 5,740,794 A * | 4/1998 | Smith et al. | 128/203.15 |
| 5,888,010 A * | 3/1999 | Laux | 401/268 |
| 6,082,356 A * | 7/2000 | Stradella | 128/203.15 |
| 6,131,288 A | 10/2000 | Westerhof et al. | |
| 6,155,454 A * | 12/2000 | George et al. | 221/25 |
| 6,238,118 B1 * | 5/2001 | Tryon | 401/153 |
| 6,241,412 B1 * | 6/2001 | Spies et al. | 401/129 |
| 6,425,888 B1 * | 7/2002 | Embleton et al. | 604/290 |
| 6,434,773 B1 | 8/2002 | Kuo | |
| 6,439,789 B1 | 8/2002 | Ballance et al. | |
| 6,697,704 B2 * | 2/2004 | Rosenblum | 700/232 |
| 6,792,945 B2 * | 9/2004 | Davies et al. | 128/203.15 |
| 6,799,571 B1 * | 10/2004 | Hughes et al. | 128/203.12 |
| 6,845,883 B2 * | 1/2005 | Pieri | 222/94 |
| 6,880,555 B1 * | 4/2005 | Brunnberg et al. | 128/203.12 |
| 6,887,709 B2 * | 5/2005 | Leong | 436/8 |
| 6,941,948 B2 * | 9/2005 | Staniforth et al. | 128/203.21 |

FOREIGN PATENT DOCUMENTS

| | | |
|---|---|---|
| DE | 19720047 A1 | 11/1998 |
| JP | 10508790 | 9/1998 |
| WO | WO 0126720 A1 * | 4/2001 |
| WO | 200241802 A1 | 5/2002 |

* cited by examiner

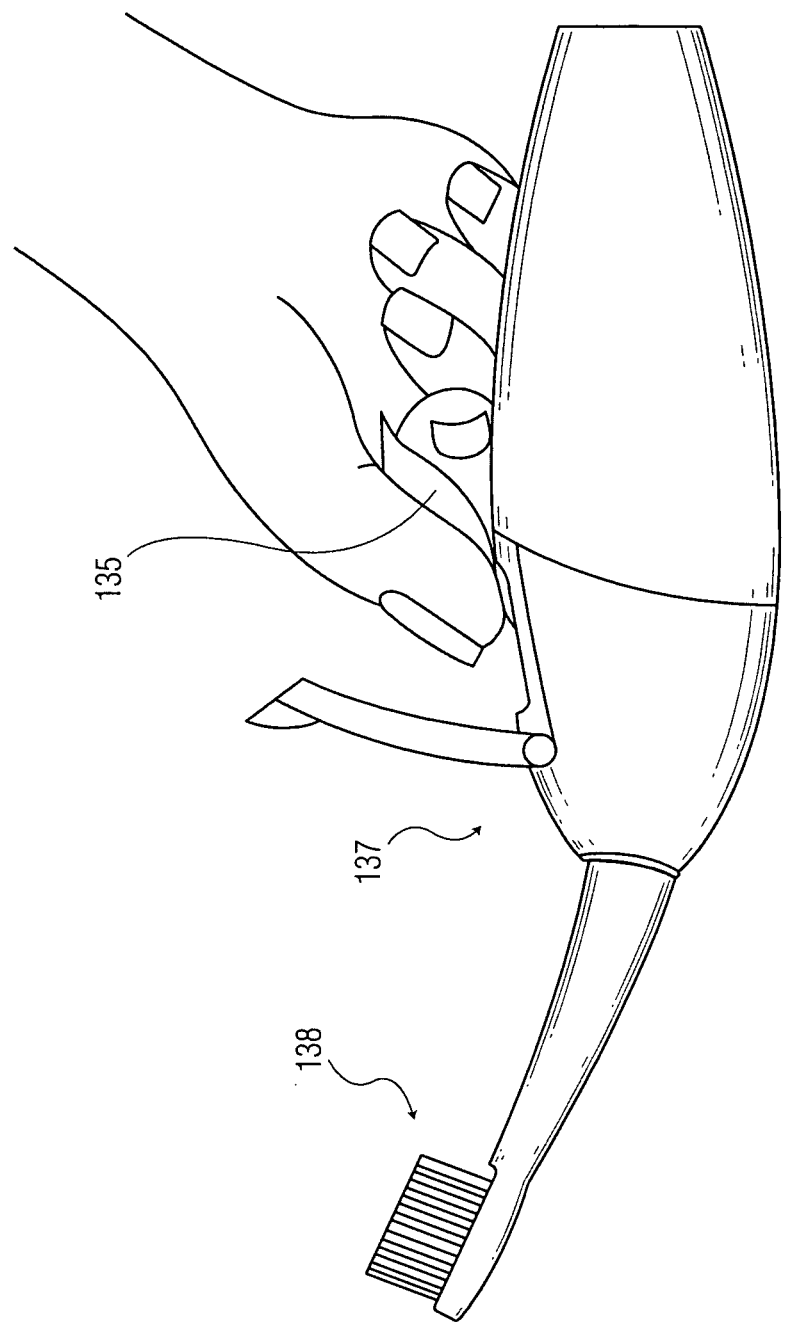

DISCRETE-AMOUNT FLUID-DISPENSING SYSTEM FOR A PERSONAL CARE DEVICE

CROSS REFERENCE TO RELATED APPLICATION

This application claims the benefit of U.S. provisional application Ser. No. 60/435,485 filed Dec. 19, 2002, which is incorporated herein by reference.

This invention relates generally to fluid-dispensing personal care appliances, such as for example, power toothbrushes, and more specifically concerns such a system in which fluid is dispensed in discrete, known amounts.

Fluid-dispensing personal care appliances of various kinds and configurations are generally well known. For instance, many toothbrushes are known which include a fluid-dispensing structure. The particular fluid will vary, depending upon the application. It can, for example, be an oral care fluid such as a dentifrice or oral medication, or a lotion for the skin. Most fluid-dispensing systems use a pump, with the user dispensing fluid through a mechanical action, although automatic fluid-dispensing devices are also known. In some arrangements, a piston or similar element is positioned within a reservoir to move fluid into a connecting line which extends to the workpiece element. In other arrangements, a peristaltic-type pump arrangement is used, in which a roller or other mechanism is operative to squeeze fluid out of a cartridge, without direct contact with the fluid. In still other arrangements, the action of the workpiece itself moves fluid from a reservoir to the workpiece.

However, many of these known fluid-dispensing devices have significant disadvantages. These disadvantages include difficulty in maintaining the various elements of the system, including in particular the pump structure itself, clean and operative. Occasionally, the fittings or other portions of the pump will dry out and/or the fluid will partially dry in the pump or the line between the pump and the workpiece, preventing proper operation until the system has been cleaned. Further, many of the known fluid-dispensing mechanisms are quite complex, and in many cases quite expensive relative to the cost of the toothbrush. Most of such fluid-dispensing devices are not reliable, particularly for long-term operation. In addition, the amount of fluid pumped can vary significantly and proper sealing of the pump system is often complex and difficult to reliably achieve.

Hence, while a fluid-dispensing capability for personal care appliances, such as a power toothbrush, is certainly known to be beneficial, very few if any such devices have been successful, even though there have been a large number of attempts.

In some cases, it is important that only a very specific amount of fluid, typically a medication, should be dispensed for a particular use event. Existing devices, as indicated above, typically do not have a high accuracy in dispensing a selected volume of fluid.

Further, it is sometimes desirable to dispense two or more medications which cannot be mixed together in a reservoir in a single use event with the medications being in prescribed, preselected amounts. To the best of applicant's knowledge, there are no currently known systems having such a capability.

Hence, it is desirable that a fluid-dispensing structure for personal care appliances have the capability of reliably dispensing discrete amounts of fluid, and also have the capability of dispensing two or more fluids at the same time to the area of interest, such as the mouth, while maintaining the fluids separate prior to dispensing.

Accordingly, the present invention in one aspect is a discrete-amount fluid-dispensing system for a personal care device, comprising: a personal care appliance having a workpiece member, such as a power toothbrush; a strip that includes a successive plurality of discrete fluid-containing packets; a compressible sealing member against which each packet on the strip may be sealed in succession; a hollow needle structure for puncturing the packets as each packet is moved in front of the needle in succession; and an actuation assembly for moving the strip against the sealing member, sealing each packet in turn against the sealing member and then compressing the sealing member, exposing the needle so that the packet is punctured by the needle, wherein continued pressure by the actuation assembly forces the fluid in the packet through the needle into a connecting line to the workpiece member.

Another aspect of the invention is a discreet-amount fluid-dispensing system for a personal care device, comprising: a personal care appliance having a workpiece member; a strip that includes a successive plurality of discrete fluid-containing packets; a needle structure on the workpiece member for puncturing the packets in succession as the strip is moved in front of the needle structure and pressure applied to the strip against the needle structure, wherein the fluid in the punctured packet thereafter flows to the vicinity of the workpiece member; and a guide structure in the appliance for holding and guiding the strip along the appliance to the vicinity of the workpiece member and then out of the appliance.

Another aspect of the invention is a discrete tablet dispensing system for a toothbrush comprising: a toothbrush having a brushhead with an opening therein; a receiving cartridge which extends along the rear of the toothbrush for receiving a plurality of dentifrice/medication tablets for oral care, wherein the forward end of the receiving cartridge has an opening which is substantially in registry with the opening in the brushhead; and an ejector mechanism associated with the receiving cartridge, which when operated ejects a tablet from the receiving cartridge into the opening in the brushhead.

Figure 1:
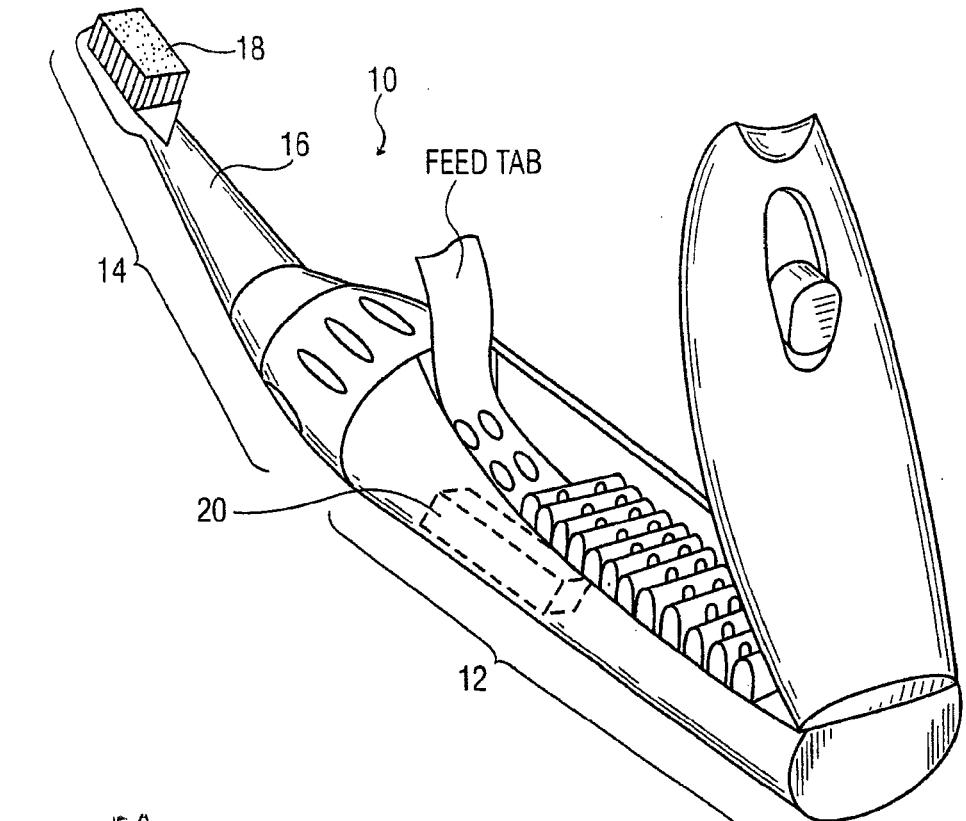
FIG. 1 is a perspective view of the fluid-dispensing system of the present invention shown in the context of a power toothbrush.
Figure 2:
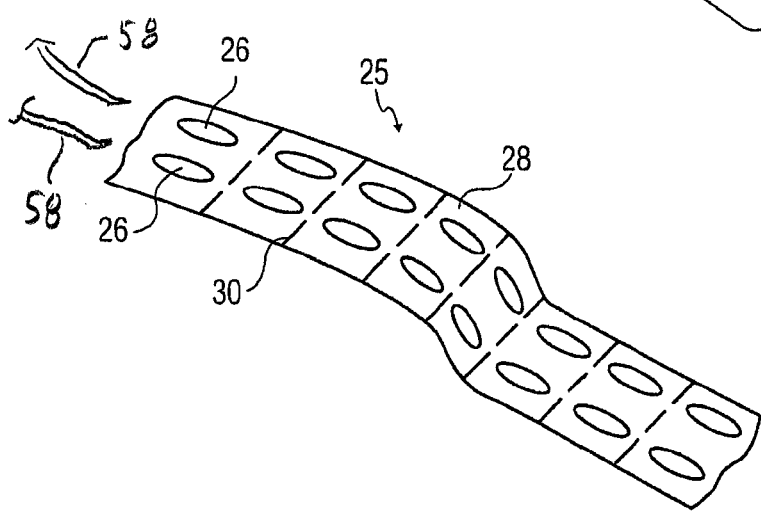
FIG. 2 shows a fluid-containing packetized strip used in the dispensing system of the present invention.

FIG. 14 shown another embodiment of the invention.

The basic structure of the present invention is shown in FIGS. 1-4, in the context of a power toothbrush application. The power toothbrush is shown generally at 10, comprising a handle portion 12 and a removable head portion 14. The head portion includes an elongated arm 16, at the end of which is a moving brushhead 18. Brushhead 18 is actuated by a driving unit 20, located in handle 12. The driving assembly can have a variety of configurations and arrangements, including but not limited to an electromagnetic actuator or a DC motor. Other arrangements can be used.

The driving unit 20 can be powered by an internal battery or from the wall. While FIG. 1 shows a power toothbrush application, it should be understood that the fluid-dispensing system of the present invention can be used in other personal care appliances. These include, for example, a shaver, a power face cleaner/brush, a hot wax hair remover, a fluid-dispensing back brush and a fluid-dispensing hair brush, among others.

The fluid-dispensing system of the present invention includes a strip or web 25 of individual packets or blisters 26-26 on a carrier element 28. Carrier element 28 is of flexible material, currently referred to as form, fill and seal packaging, such as triophane, polypropylene or fibrous web, and includes perforation lines 30-30 between each successive packet 26. Fluid is contained within packets 26. "Fluid" is intended herein to be a broad term, including a variety of substances, having a range of viscosities, including gels. Fluid will include dentifrices and medications, as well as various lotions.

The type of fluid will vary in accordance with the particular application. It can be a conventional dentifrice, for instance, for a power toothbrush application, or particular medications useful in the oral cavity for the treatment of gum disease or other oral disease. The particular fluid can be such as to aid the action of the device, such as fluid which assists in the shaving process, or which soothes the skin for other skin-related applications. Strip 25, in the embodiment shown, shows successive rows of two side-by-side packets 26. The packets, for instance, could contain two or more different medications which cannot be mixed together in a single reservoir or in a single packet, but which need to be dispensed for the same treatment event. Typically, however, each row will include only a single packet.

Figure 3:
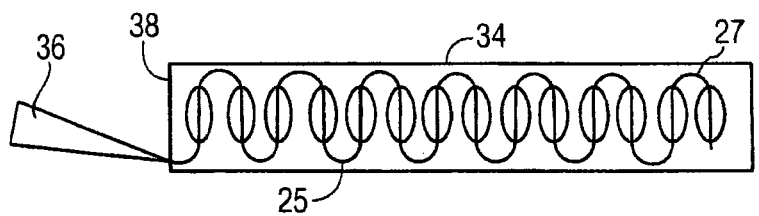
FIG. 3 is a cartridge for the fluid-containing strip.

The strip 25 of packets will typically be folded in a serpentine arrangement and into a cartridge 34, such as shown in FIG. 3 or rolled into a round package. A start feed tab 36 extends out the front end 38 of cartridge 34. Near the rear end of strip 25, a visual marker 27 can be provided which indicates that the end of the strip is near.

Figure 4:
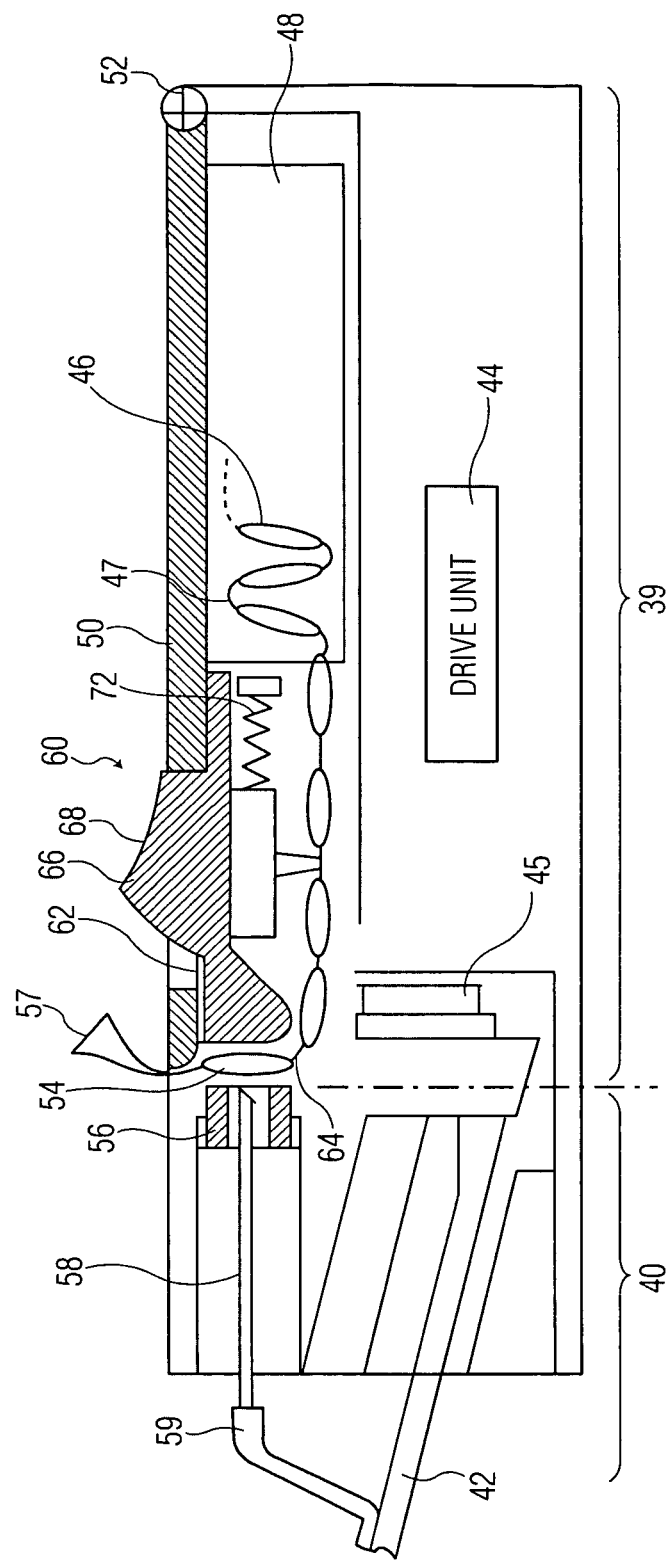
FIG. 4 is a cutaway view of the fluid-dispensing system of the present invention in a power toothbrush application.
Figure 5:
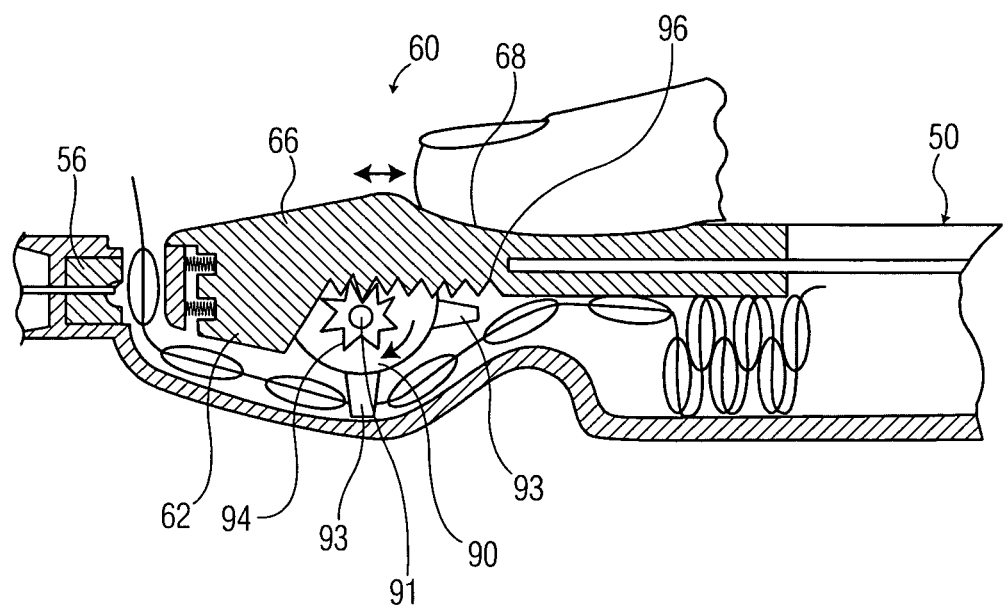
FIG. 5 is a cutaway view showing a portion of the structure of FIG. 4.
Figure 6:
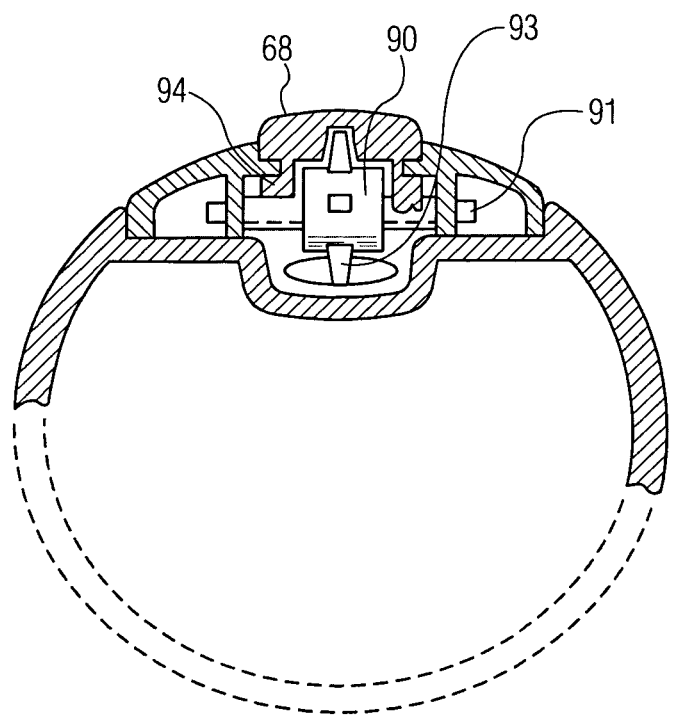
FIG. 6 is a cross-sectional view along lines 6-6 in FIG. 5.

FIGS. 4, 5 and 6 show the details of the fluid-dispensing system of the present invention, again for a power toothbrush application for ease and clarity of explanation. The power toothbrush 38 includes a handle portion 39 and a separate, removable head portion 40. A drive shaft 42 for a brushhead (not shown) is driven by a driving unit 44 assembly which is an electromagnetic driver in the embodiment shown, operating on magnets 45 at the rear end of drive shaft assembly 42. Such structure is described in detail in U.S. Pat. No. 5,189,751. A cartridge 46 containing a strip/web 47 of fluid-containing packets is shown in a cartridge-receiving portion 48. To access the cartridge-receiving portion 48, a panel 50 on the handle is lifted up and rotated about hinge 52.

In use of the appliance, a cartridge 46 is inserted into the handle and a forward tab portion 57 of strip 47 is pulled out of the cartridge 46 sufficiently that a first packet 54 in the strip is positioned against a sealing member 56 located at the rear of head portion 40. Sealing member 56 is a hollow cylinder, typically made out of a compressible, resilient material, such as rubber or plastic backed by a spring. The sealing member 56 in the embodiment shown has an outside diameter of approximately 0.3 inches and an inside diameter of approximately 0.1 inches, and is approximately 0.3 inches high. A hollow needle 58 is mounted to extend through the center of the sealing member. The hollow needle is connected to a fluid line 59 which extends to the workpiece (not shown), such as a brushhead.

The fluid-dispensing assembly 38 also includes an actuation assembly 60. Actuation assembly 60 includes a piston element 62 having a front face 64 which is in substantial registry with a rear face of sealing member 56. Extending rearwardly from piston element 62 is a control element 66 which has an upper surface 68 which is curved to match a user's thumb. Control element 66 extends slightly above the exterior surface of panel 50, which has an opening therein to accommodate the control element and its forward movement.

Actuation assembly 60 is mounted within the toothbrush for movement in the direction of the sealing member 56 by action on the control element 66. Forward movement of the actuation assembly is accomplished by the pressure of a user's thumb on the control element in the forward direction. When the user releases the thumb pressure, a return spring 72 returns the actuation assembly to its rear position within handle 34.

Figure 7:
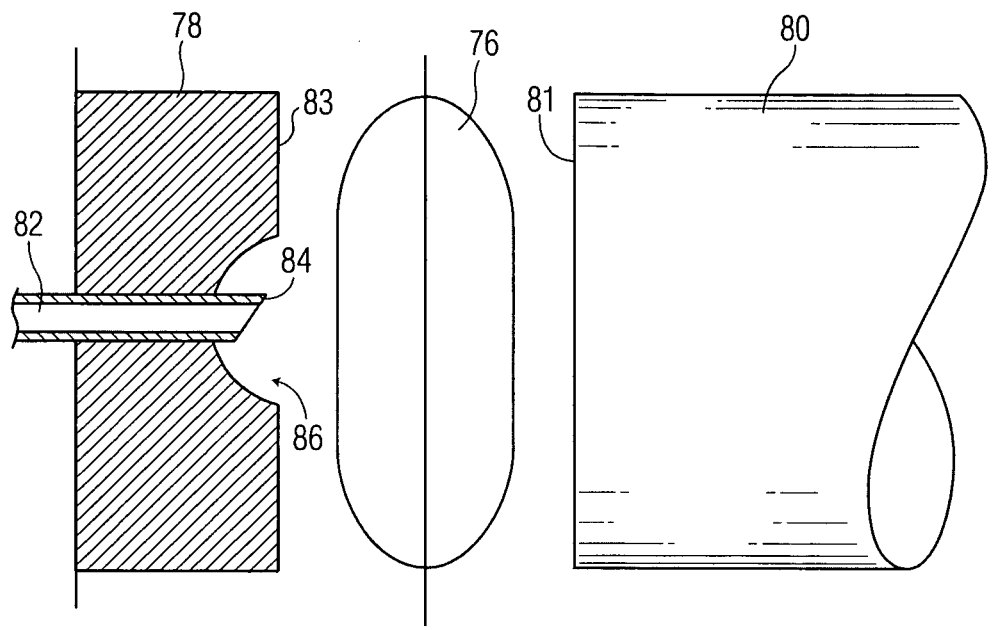
FIGS. 7, 8 and 9 are cutaway views showing the sequence of operation of the fluid-dispensing system of the present invention.
Figure 8:
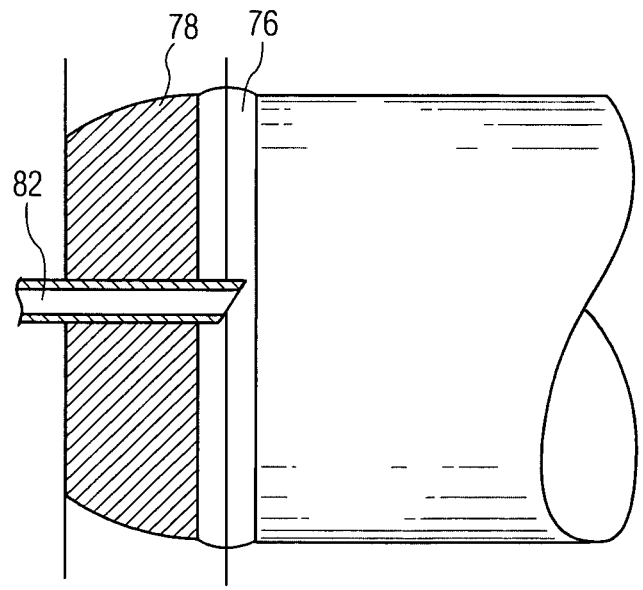
Figure 9:
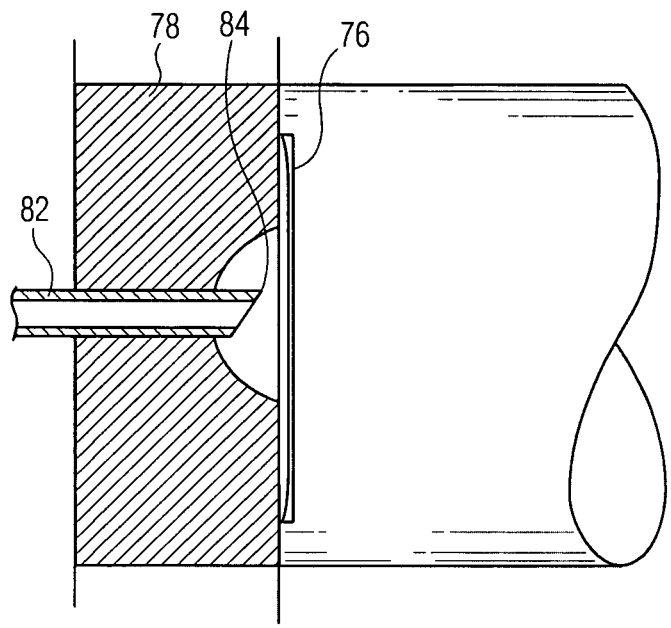

FIGS. 7, 8 and 9 show the steps in dispensing fluid by means of the system shown and described. FIG. 7 shows a single fluid-filled packet 76 positioned between sealing member 78 and piston 80. In this position, there is usually a small space between forward surface 81 of piston 80 and packet 76, as well as a space between packet 76 and rear surface 83 of sealing member 78. Hollow needle 82, which extends through the center of sealing member 78, is angled and sharpened at its tip 84 in order to facilitate puncture of packet 76. The center portion of the sealing member 78 has a scooped-out region 86, into which tip 84 of the needle extends, but not beyond surface 83 when the sealing member is in its relaxed condition (FIG. 7).

When the user pushes forward on the control member 66 (FIG. 5) to the extent shown in FIG. 8, packet 76 is compressed between sealing member 78 and piston 80. When packet 76 initially makes contact with sealing member 78, a fluid-tight seal is accomplished therebetween. Sealing member 78 compresses, such that stationary needle 82 extends beyond surface 83 of the sealing member, penetrating packet 76, which is also compressed.

FIG. 9 shows packet 76 fully compressed, with substantially all of the fluid in the packet having been forced out of the packet by the action of the piston, into needle 82 and, from there through the connecting line and to the workpiece. The individual components in the system are shaped and arranged so that the packet is substantially completely emptied once the packet has been punctured and pressure has been maintained for a suitable period of time, allowing the sealing member to expand into space formerly occupied by the packet with fluid.

After dispensing has been completed, the pressure on the thumb actuated control element 66 is released, the sealing member returns to its original configuration, and the actuation assembly 60 returns to its rear position.

In the embodiment shown, a single needle has been described and shown for puncturing a single packet. A single connecting line connects the needle with the workpiece. In the embodiment where two packets are side-by-side in each successive row (FIG. 2), two adjacent needles are used, which puncture the individual packets simultaneously. The two needles will connect to connecting lines, which could be joined early, forming a single connecting line, or there could be two separate connecting lines up to the workpiece. Alternatively, multiple packets could be dispensed in a short sequence. Two successive actuation actions could be used to dispense the two (or more) fluids to the workpiece.

Hence, the present structure provides for the simultaneous dispensing, if desired, of two or more fluids which are not compatible for storage in a single reservoir. This is advantageous for those situations where more than one fluid must be provided to the user in the course of a single treatment event.

FIGS. 5 and 6 show a structure for advancing the strip of packets after each use. A drive wheel 90 is mounted for rotation on an axle 91 on the actuation assembly. The drive wheel 90 includes cogs 93 which extend out from the periphery of the drive wheel 90 and are designed to engage the surface of the strip of packets between successive packets as the drive wheel is rotated. Mounted on drive wheel 90 is a sprocket member 94 which mates with a rack element 96 of the actuation assembly. Drive wheel 90 includes a one-way clutch which allows it to move only in a clockwise motion. As the actuation assembly is moved forward, compressing the packet against the sealing member 56, the rack 96 engages the sprocket member 94, but there is no rotation of the drive wheel. On the return of the actuation assembly, drive wheel 90 is engaged by the clutch and turns, engaging the packet strip with cogs 93, bringing the next packet into position between the piston and the sealing member and moving the depleted packet out of the appliance.

Each depleted packet, in turn, as it comes outside of the appliance, is removed at a perforation line between the depleted packet and the packet now in position for dispensing. Alternatively, the depleted packets can be accumulated in a cartridge or the like.

Hence, a fluid such as a dentifrice can be accurately dispensed in discrete, known amounts, because the amount of fluid in each packet is controlled and hence known, as successive packets are brought into position between the piston and the sealing member. The creation of a seal between the packet and the sealing member prior to puncture results in a clean delivery of fluid, with fluid in the packet going through the needle to the workpiece, and without any fluid escaping between the sealing member and the packet being emptied. The mechanical structure shown and described results in a reliable puncturing and dispensing action for an extended number of uses. The actuation assembly also includes a spring structure returning the actuation assembly to its rear (rest) position after dispensing of the fluid in one packet has been accomplished. During the return time, a drive mechanism is activated to bring the next packet into position between the piston and the sealing member. A motor could be used to automatically move the strip, compress the packet and sealing member with the piston and dispense the fluid.

In a variation of the above embodiment, individual separate fluid-containing packets (not associated with a strip) could be loaded by a user into a chamber which contains structure similar to that described above to seal, puncture and deliver the fluid from the individual packet to a workpiece, such as a brushhead.

Figure 10A:
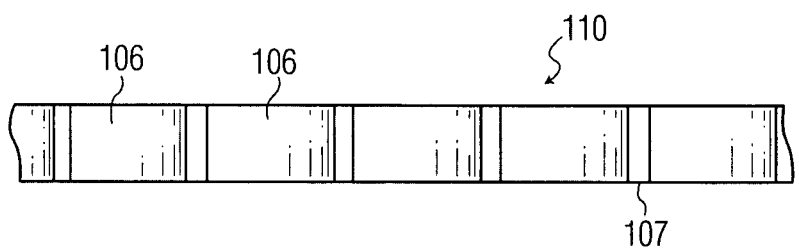
FIG. 10 is a cutaway view of one alternative embodiment of the structure of FIGS. 1-9.
Figure 10B:
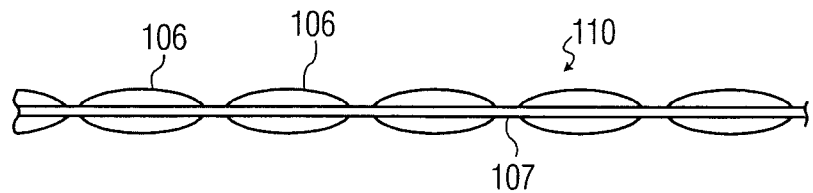
Figure 10C:
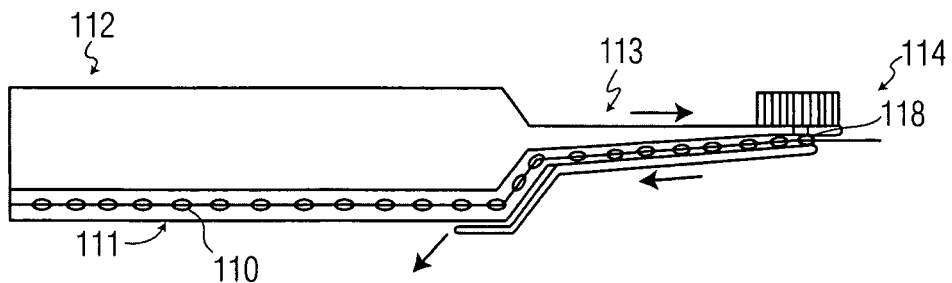
Figure 10D:
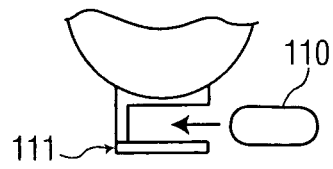

FIGS. 10a-10d show one alternative embodiment to the system of FIGS. 1-9. The fluid is stored in packets 106 on prefabricated foil strips 110, with hot seals 107 between the packets. Foil strip 110 is inserted into a guide portion 111 of the toothbrush. As shown in FIG. 10(c), the strip 110 extends through a front part 113, i.e. head portion, of the brush, up to the brushhead 114, and then reverses direction rearwardly 180° at the brushhead. The strip continues to the rear and then out of the toothbrush near the front end of the handle.

To move or transport the strip 110 simply requires the user to pull to the rear on the exposed strip, moving the strip in the direction of the arrow. Depleted packets may be removed by the means of tearing the strip at perforations, cutting or any other means, between successive packets. The brushhead 114 includes a needle or sharp edge 117, past which the strip extends. Placing pressure on the strip in this vicinity results in a puncture of the packet and forcing of the dentifrice through an opening 118 in the brushhead base into the bristles of the toothbrush. Again, as in the other embodiments, fluid is dispensed in discrete amounts contained in individual packets on a transporting strip. The amount in each packet is known.

Figure 11:
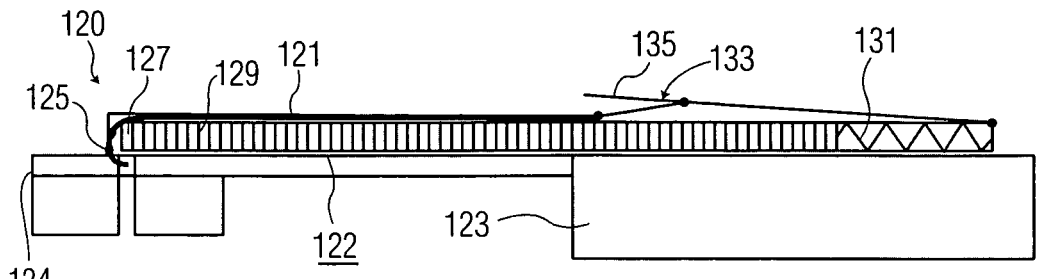
FIG. 11 is a cutaway view showing another alternative embodiment of the structure of FIGS. 1-9.

FIG. 11 shows another embodiment, in which a toothbrush 120 includes a cartridge 121, which is mounted to a rear surface 122 of the toothbrush, extending from handle 123 to brushhead 124. Brushhead 124 has a central opening 125 which is in registry with an opening 127 in cartridge 121 at a forward end thereof. A plurality of individual tablets 129-129 is provided in the cartridge, spring-loaded by means of a spring 131. Spring 131 pushes the tablets to the forward end of the cartridge. The apparatus includes a dispensing actuator 133, which is mechanically arranged so that operation of the actuator, such as by a downward action on portion 135 thereof, presses the tablet at the forward end of the cartridge through opening 127 in the cartridge and opening 125 in the brushhead. The tablet moves by gravity through the brushhead into the mouth of the user. Again, the dentifrice/medication in the tablet is dispensed individually in discrete, known amounts. In this embodiment, the separate tablets are arranged sequentially and are separate, i.e. they are not joined by a transport web.

Accordingly, a fluid-dispensing system has been disclosed in which known amounts of fluid are dispensed for a given treatment event. Control is maintained over the amount of fluid provided to the user. Sterility is also maintained, both with sterile packets and the use of a sealing member during dispensing of the fluid. The cartridge containing the strip of packets can be easily removed and inserted into an appliance by opening a cover portion in the appliance handle. Dispensing the individual discrete amounts of fluid can be either manual, such as by a user, or can be automatic with a motor of some kind. Further, multiple packets can be arranged in a single row on the strip, providing more than one fluid/medication to be dispensed for one treatment event. High control is thus maintained over the dispensing of fluid with the arrangement shown.

As indicated above, the fluid-dispensing system can be used in a variety of personal care hygiene devices, including power toothbrushes, electric shavers and other devices mentioned above.

In a variation of the fluid-containing packet strip described above, a strip may be divided into individual portions where each strip portion is consumable in its entirety. A dentifrice/medication may comprise the individual portions or may be contained in each portion with the strip portion being consumable in addition to the fluid-medication container therein. In such an arrangement, shown in FIG. 14, there is no remaining strip element or depleted package to be thrown away. The fully ingestible element could be in the form of a strip 135 or a rod, or other form, in a toothbrush 137 from which pieces of known dentifrice/medication amounts are cut and used/dispensed. The individual sections can be presented manually to the user as shown, or can be directed to the vicinity of the brushhead 138.

Figure 12:
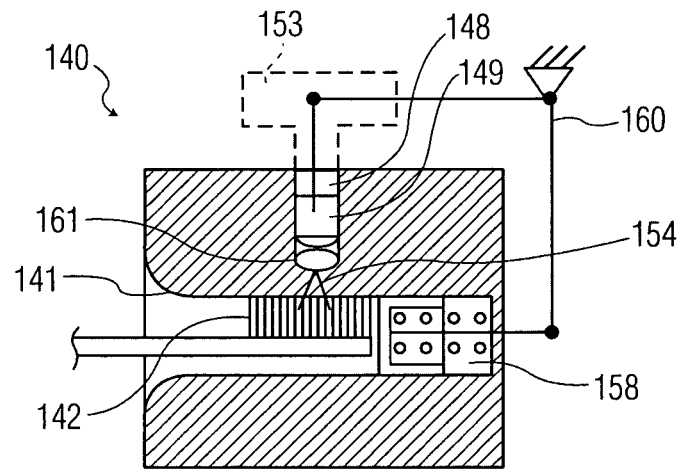
FIGS. 12 and 13 show another embodiment of the invention.
Figure 13:
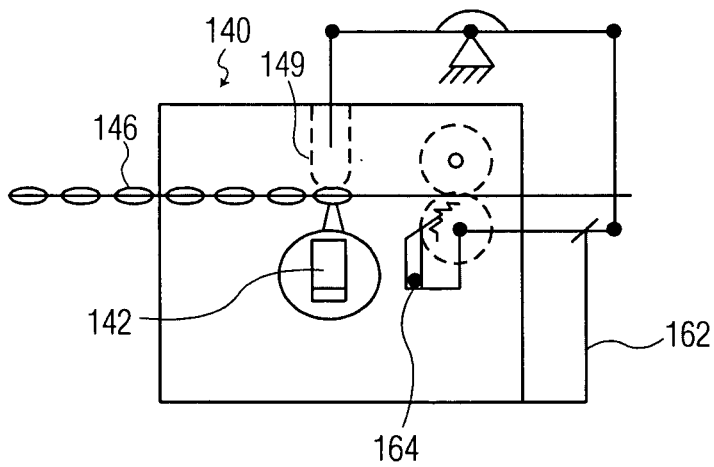

FIGS. 12 and 13 show another embodiment of the present invention, in which a fluid dispensing system using fluid-filled discrete packets on a strip, with the packets having a known quantity of fluid therein, is separate from the appliance, which could for instance be a toothbrush. In this embodiment the fluid dispensing system comprises a separate unit 140, as opposed to being a part of the appliance. It could also be part of a charging unit for the appliance.

The unit 140 includes an opening 141 to receive a workpiece portion, such as a brushhead 142 of a power toothrbush appliance. A strip 146 of fluid-filled packets is positioned in a slot 148 in unit 140, above opening 141. A plunger 149 is located above strip 146. Positioned below the strip is a needle 154. When brushhead 142 is inserted into opening 141, it engages a spring 158 which through a lever 160 activates the plunger 149 forcing a packet 161 located beneath the plunger down against the needle 154. The plunger could also be activated by a knob 153 or by a small motor. The fluid in the punctured packet falls through an opening in the unit onto brush 142. When the plunger 149 is released by removal of the brushhead, lever 162 and associated cam 164 transports the strip by one packet for the next dispensing event. The depleted packet moves out of unit 140. As with the other embodiments, there may be more than one fluid dispensed for a particular event, such as with the use of multiple packets.

Although a preferred embodiment of the invention has been described for purposes of illustration, it should be understood that various changes, modification and substitutions may be incorporated in the embodiment without departing from the spirit of the invention which is defined in the claims which follow.

The invention claimed is:

1. A discrete-amount fluid-dispensing system for use in a personal care appliance, comprising:
    a personal care appliance having a workpiece member;
    a strip which includes a successive plurality of discrete fluid-containing packets;
    a compressible sealing member against which each packet on the strip is sealed in succession;
    a hollow needle structure for puncturing the packets as each packet is moved in front of the needle in succession; and
    an actuation assembly for moving the strip against the sealing member, sealing each packet in turn against the sealing member and then physically compressing the sealing member, exposing the needle so that the packet is punctured by the needle, wherein continued pressure by the actuation assembly against the packets forces the fluid in the packet through the needle and into a connecting line to the workpiece member.

2. A system of claim 1, wherein each packet contains a known amount of fluid.

3. A system of claim 1, including two packets side-by-side in successive rows on the strip and two adjacent needles for dispensing fluid for the two packets simultaneously.

4. A system of claim 1, wherein the strip includes a line of perforations between successive packets thereon.

5. A system of claim 1, including an ejector mechanism which when activated advances the strip one packet, moving a next packet in front of the sealing member.

6. A system of claim 1, wherein the sealing member is compressible and resilient member and has a scooped out center section into which a tip of the hollow needle extends.

7. A system of claim 1, wherein the actuation assembly includes a piston element which in operation of the actuation assembly presses the packet against the sealing member for sealing therebetween and then against the needle for puncture of the packet, as the sealing member comprises, and further includes a control portion which extends slightly above a surface of the appliance for convenient manual action.

8. A system of claim 1, wherein the personal care appliance is a power toothbrush.

9. A system of claim 1, including a cartridge member to house the strip of packets, wherein the appliance includes a receiving portion for receiving the cartridge.

10. An appliance for personal use, comprising:
    a personal care appliance having a workpiece;
    a discrete-amount substance-dispensing system in the personal care appliance, the substance-dispensing system including a strip which includes a successive plurality of discrete-amount substance-containing packets;
    a hollow puncture element, activated by a manually operated control element, for puncturing the packets as each packet is moved in front of the puncture element in succession; and
    a system for applying mechanical pressure directly to a surface of the packet, following puncture of the packet, to reduce the volume of the packet, forcing the substance in the punctured packet out of the packet through the puncture element through a connecting line to the workpiece, wherein the puncture element and the system for applying mechanical pressure move sequentially for each packet in turn from a first position in which they are relatively away from the packet and a second position in which they are in contact with the packet, in order to puncture and apply said mechanical pressure to the surface of the packet.

* * * * *